(12) United States Patent
Chiang et al.

(10) Patent No.: US 10,106,433 B2
(45) Date of Patent: Oct. 23, 2018

(54) METAL OXIDE NANOPARTICLE MATERIAL

(71) Applicant: National Central University, Jhongli, Taoyuan County (TW)

(72) Inventors: Anthony Shiaw-Tseh Chiang, Jhongli (TW); Sho-Hsun Wang, Jhongli (TW); Chin-Tung Pai, Jhongli (TW); Chien-Wei Chen, Jhongli (TW)

(73) Assignee: NATIONAL CENTRAL UNIVERSITY, Jhongli, Taoyuan County (TW)

( * ) Notice: Subject to any disclaimer, the term of this patent is extended or adjusted under 35 U.S.C. 154(b) by 11 days.

(21) Appl. No.: 14/948,590

(22) Filed: Nov. 23, 2015

(65) Prior Publication Data

US 2016/0096738 A1    Apr. 7, 2016

Related U.S. Application Data

(62) Division of application No. 14/525,452, filed on Oct. 28, 2014.

(30) Foreign Application Priority Data

May 13, 2014 (TW) .............. 103116857 A (51) Int. Cl.
*C01G 25/02* (2006.01)
*B01J 13/00* (2006.01)
*C07F 7/00* (2006.01)

(52) U.S. Cl.
CPC .......... *C01G 25/02* (2013.01); *B01J 13/0047* (2013.01); *C07F 7/006* (2013.01); *C01P 2002/54* (2013.01); *C01P 2002/72* (2013.01); *C01P 2002/82* (2013.01); *C01P 2002/86* (2013.01); *C01P 2004/64* (2013.01); *C01P 2004/80* (2013.01); *C01P 2006/12* (2013.01); *Y10T 428/2982* (2015.01)

(58) Field of Classification Search
CPC ....... C01G 25/02; C07F 7/006; B01J 13/0047
See application file for complete search history.

(56) References Cited

U.S. PATENT DOCUMENTS

| 5,635,154 A | 6/1997 | Arai et al. |
| 6,376,590 B2 | 4/2002 | Kolb et al. |
| 7,393,518 B2 | 7/2008 | Chiang et al. |
| 7,553,474 B2 | 6/2009 | Ohmori et al. |

(Continued)

FOREIGN PATENT DOCUMENTS

| CN | 1552517 | 12/2004 |
| CN | 102765755 | 11/2012 |

(Continued)

OTHER PUBLICATIONS

Pai, Preparation of dispersible c-ZrO2 nanocrystals, Sep. 11, 2012, http://ir.lib.ncu.edu.tw,—, Entire Document.*
English translation of abstract of TW I401287 (published Jul. 11, 2013).
English translation of abstract of TW I252215 (published Apr. 1, 2006).

(Continued)

*Primary Examiner* — James Fiorito
(74) *Attorney, Agent, or Firm* — McClure, Qualey & Rodack, LLP (57) ABSTRACT

A zirconia nanoparticle material includes a zirconia nanoparticle and a carbonate coordinated on a surface of the zirconia nanoparticle. The carbonate is 1 to 10 parts by weight of the zirconia nanoparticle.

5 Claims, 8 Drawing Sheets

(56) References Cited

U.S. PATENT DOCUMENTS

| | | |
|---|---|---|
| 7,629,389 B2 | 12/2009 | Ohmori et al. |
| 7,691,910 B2 | 4/2010 | Ohmori et al. |
| 7,985,476 B2 | 7/2011 | Kurino et al. |
| 8,512,464 B2 | 8/2013 | Joly et al. |
| 2012/0071680 A1 | 3/2012 | Tokumitsu |

FOREIGN PATENT DOCUMENTS

| | | |
|---|---|---|
| TW | 200301225 | 7/2003 |
| TW | I252215 | 4/2006 |
| TW | 200630426 | 9/2006 |
| TW | 200704680 | 2/2007 |
| TW | I382961 | 1/2013 |
| TW | I389849 | 3/2013 |
| TW | 201328981 | 7/2013 |
| TW | I401287 | 7/2013 |

OTHER PUBLICATIONS

English translation of abstract of TW I382961 (published Jan. 21, 2013).

English translation of abstract of TW I389849 (published Mar. 21, 2013).

English translation of abstract of TW 200630426 (published Sep. 1, 2006).

English translation of abstract of TW 200704680 (published Feb. 1, 2007).

English translation of abstract of TW 201328981 (published Jul. 16, 2013).

English translation of abstract of CN 102765755 (published Nov. 7, 2012).

Chin-tung Pai, "Preparation of dispersible c-ZrO2 nanocrystals", National Central University Institutional Repository, available Sep. 11, 2012.

* cited by examiner

METAL OXIDE NANOPARTICLE MATERIAL

RELATED APPLICATIONS

The present application is a divisional application of U.S. application Ser. No. 14/525,452 filed Oct. 28, 2014, which claims priority to Taiwanese Application Serial Number 103116857, filed May 13, 2014. The entire disclosures of all the above applications are hereby incorporated by reference herein.

BACKGROUND

Field of Invention

The invention relates to a metal oxide nanoparticle material, and more particularly, to a zirconia nanoparticle and preparation method thereof.

Description of Related Art

Zirconia is widely applied in refractory materials, ceramic appliances and fuel cells for its well heat tolerance and ability of oxygen conductance. Further, zirconia particles with high specific surface area are frequently used as solid catalyst or catalyst support in petrochemical industry. In these applications, using crystalline zirconia nanoparticles can increase the specific surface area and reduce the sintering temperature.

Furthermore, the refractive index and the hardness of zirconia are much higher than that of silicone oxide. Composite of zirconia nanoparticles and organic resins leads to a high refractive index and hardness while keeping a good optical transmittance. The refractive index of the composite is decided by the loading and the crystallinity of the zirconia nanoparticles, while the optical transmittance of the composite depends on the particle size and the aggregation state of the zirconia nanoparticles. For example, adding crystalline zirconia nanoparticles can significantly increase the refractive index of the composite, while the increase will be limited when adding amorphous zirconia nanoparticles. Also, the optical transmittance of the composite is better when adding small and aggregation-free crystalline zirconia nanoparticles, but reduced if the zirconia nanoparticles are large or aggregated. Further, the loading capacity of the zirconia nanoparticles in the organic resins depends on the aggregation state and the aspect ratio of the particles. The loading capacity decreases with increasing particle aggregation, and also with increasing particle aspect ratio.

There are three crystalline structures for zirconia, the monoclinic, the tetragonal and the cubic phases. Generally, the zirconia is in monoclinic phase at room temperature. However, due to the high surface energy, it is possible to keep the crystal in cubic or tetragonal phase even at room temperature if the size of crystalline zirconia nanoparticles is less than 10 nm. With the increase of temperature, the zirconia is subjected to phase transformation from the monoclinic phase to the tetragonal phase at 1170° C., and from the tetragonal phase to the cubic phase at 2370° C. The zirconia transforms from the cubic phase back to the monoclinic phase when cooling down to the room temperature. Since the monoclinic phase has a lower density than that of the high-temperature phases, volume expansion occurs during the cooling and introduces enormous stress resulting in the formation of cracks in the zirconia body. To avoid the phase transformation, calcium, magnesium, strontium, yttrium and related elements are usually added to stabilize the tetragonal or cubic phase zirconia upon decreasing temperature. The aspect ratio of the cubic and the tetragonal phase are usually lower than that of the monoclinic phase. When adding zirconia nanocrystals into an organic resin, the addition of cubic or tetragonal phase has a lower impact on the viscosity of the organic resins. In comparison, the viscosity of the composite quickly increases when adding nanoparticles of monoclinic zirconia having a higher aspect ratio. This significantly limits the amount of zirconia nanoparticles that can be added into the organic resins. Because cubic phase zirconia nanoparticles have the highest symmetry and lowest aspect ratio among the phases, it is desirable to prepare small, non-aggregated, highly-crystalline cubic-phase zirconia nanoparticles.

The zirconia nanoparticles may be fabricated by physical or chemical methods. Since the chemical method is much simpler and cheaper, it has been the favorable method for preparing zirconia nanoparticles. However, due to particle aggregation and insufficient crystallinity, it is difficult to obtain non-aggregated and highly-crystalline zirconia nanoparticles with monomodal size distribution. Further, general methods employed to prepare zirconia nanoparticles usually produce a mixed phases of monoclinic, tetragonal and cubic phases. For example, U.S. Pat. No. 6,376,590 describes the preparation of the zirconia sols without adding a crystal phase stabilizer. The zirconia nanoparticles have an average primary particle size about 20 nm, a crystallinity index of about 70%, and are a combination of cubic and tetragonal phases. TW Patent No. 1401287 describes a transparent dispersion having zirconia nanoparticles of tetragonal phase.

When the zirconia nanoparticles produced by the chemical method are applied to prepare ceramic slurry or to compound with an organic resin, the particle surface must be modified for the dispersion in water or organic solvent. Organic surfactants, chelating agents or surface modifiers are applied on the surface of the zirconia nanoparticles to prevent them from aggregation, so that a stable dispersion or sol in the target solvent can be achieved. Many of the chemical methods for producing zirconia nanoparticles have been done in the presence of organics. The organics may be the surfactant, the chelating agents or even the solvent. It may also come from the reaction media or the zirconium precursor. This produced a large quantity of organic contaminated waste after recovering the product.

If the ligand on the surface of the zirconia nanoparticles does not match the solvent in the target application, a secondary process is required to remove the ligand, and replacing it with another more appropriate one. However, replacing a strong ligand may be both time- and energy-consuming, which significantly deteriorates the efficiency of the process.

To assure their dispersion, the zirconia nanoparticles in the market are generally stored in the form of a sol or a suspension. After the removal of the solvent, the zirconia nanoparticles usually aggregate and fail to be dispersed back into the original solvent. Therefore, it is required to store and transport the zirconia nanoparticles in the sol form.

SUMMARY

The invention provides a zirconia nanoparticle material to solve the deficiency of traditional zirconia nanoparticles. The zirconia nanoparticle material can be stored in the solid form. The surface is covered with a weak ligand that can be easily exchanged with the proper ligand to make it dispersible in different solvents.

An aspect of the invention is to provide a zirconia nanoparticle material. The zirconia nanoparticle material includes a zirconia nanoparticle with carbonate coordinated on a surface of the zirconia nanoparticle. The carbonate is 1 to 10 parts by weight of the zirconia nanoparticle.

In one or more embodiments, calcium, magnesium, yttrium, titanium, aluminum, cerium or lanthanide is doped in the zirconia nanoparticle, which a molar ratio of the doped element to zirconium is smaller than 0.2.

In one or more embodiments, a particle size of the zirconia nanoparticle is in a range from about 1 nm to about 10 nm.

In one or more embodiments, a crystalline phase of the zirconia nanoparticle is in monoclinic phase, tetragonal phase, cubic phase or a combination thereof.

In one or more embodiments, the crystalline phase of the zirconia nanoparticle is in pure cubic phase.

Another aspect of the invention is to provide a method of preparing a zirconia nanoparticle material. An organic-free solvent is provided, and a precursor is dispersed in the organic-free solvent to obtain an aqueous mixture. The precursor includes a hydroxide or a salt of zirconium and a hydroxide or a salt of sodium, which at least one of zirconium and sodium is a carbonate. The aqueous mixture is heated at about 90° C. to about 120° C. for about 4 hours to 12 hours, and solids in the aqueous mixture are recovered to obtain zirconia nanoparticles having carbonate coordinated thereon.

In one or more embodiments, the hydroxide or the salt of zirconium is zirconium carbonate, zirconium hydroxide, or a combination thereof, and the hydroxide or the salt of sodium is sodium hydroxide, sodium carbonate, sodium orthozirconate, or a combination thereof.

In one or more embodiments, a molar ratio of the sodium to the carbonate is no less than 2.6.

In one or more embodiments, the solid in the aqueous mixture is recovered by separating the solids from the aqueous mixture. The solids are washed with water, acetone, carbonic acid, ammonium bicarbonate, or a combination thereof, and then dried.

In one or more embodiments, the carbonate on the zirconia nanoparticles is further replaced with an organic ligand or an inorganic ligand to make it dispersible in a desired solvent.

It is to be understood that both the foregoing general description and the following detailed description are but examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Reference will now be made in detail to the embodiments of the invention, examples of which are illustrated in the accompanying drawings. Wherever possible, the same reference numbers are used in the drawings and the description to refer to the same or like parts.

When a surface of a metal oxide particle is modified by a ligand, this modification step is known as "coordination". When ligand coordinates on the metal oxide particle, the ligand provides a lone pair to an empty orbital of the metal center, and a coordination bond is formed. The bond strength of the coordination bond is similar to a covalent bond. Therefore, replacing the ligand on the surface of the metal oxide particle begins with breaking the coordination bond between metal center and the ligand, and a new ligand could be coordinated on the surface of the metal oxide particle.

Because the bond strength of the coordination bond is similar to the covalent bond, breaking a strong coordination bond is both time- and energy-consuming. Therefore, the present disclosure provides a zirconia nanoparticle material. The zirconia nanoparticle material includes a zirconia nanoparticle and a weak carbonate ligand. The carbonate is weakly coordinated on the surface of the zirconia nanoparticle and being 1 to 10 parts by weight of the zirconia nanoparticle.

The zirconia nanoparticle may also be doped with an element of calcium, magnesium, yttrium, titanium, aluminum, cerium or a lanthanide to enhance stability. With doping of these elements, the zirconia nanoparticle could maintain as cubic phase after high temperature treatment, and the utilization of the zirconia nanoparticle is more versatile therefore. A molar ratio of the doped element to zirconium element of the zirconia nanoparticle is smaller than 0.2.

Because the carbonate is a weak ligand, other ligand could easily replace the carbonate to coordinate on the surface of the zirconia nanoparticle. For example, stronger organic acid replaces the carbonate and coordinates on the surface of the zirconia nanoparticle while releasing carbon dioxide. Such organic ligand makes the zirconia nanoparticle dispersible in different solvents for desired applications.

Figure 1:
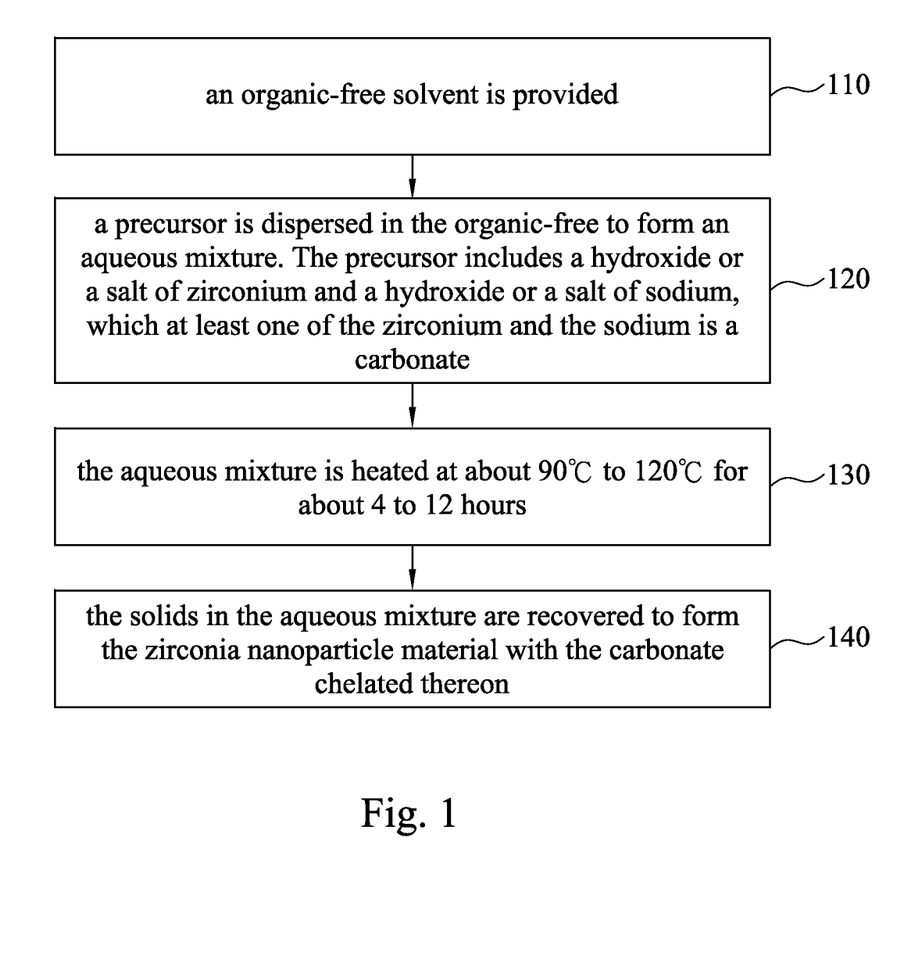
FIG. 1 is a process of preparing a zirconia nanoparticle material, in accordance with various embodiments.

Please refer to FIG. 1, FIG. 1 is a process of manufacturing the zirconia nanoparticle material. Referring to operation 110, an organic-free solvent is provided, which is water. Continuing to operation 120, a precursor is dispersed in the solvent to form an aqueous mixture. The precursor includes a hydroxide or a salt of zirconium and a hydroxide or a salt of sodium, which at least one of the salts of zirconium and the sodium is a carbonate. The hydroxide or the salt of zirconium is zirconium carbonate, zirconium hydroxide, or a combination thereof, and the hydroxide or the salt of sodium is sodium hydroxide, sodium carbonate, sodium orthozirconate, or a combination thereof.

In some embodiments, the hydroxide or the salt of zirconium is zirconium carbonate, and the hydroxide or the salt of sodium is sodium hydroxide. In other embodiments, the hydroxide or the salt of zirconium is zirconium hydroxide, and the hydroxide or the salt of sodium is sodium carbonate.

The zirconium is 5 to 20 parts by weight of the aqueous mixture; the carbonate is 0.5 to 4 parts by weight of the aqueous mixture; and the sodium is 4 to 15 parts by weight of the aqueous mixture. A molar ratio of sodium to the carbonate is no less than 2.6.

Continuing to operation 130, the aqueous mixture is heated at about 90° C. to 120° C. for about 4 to 12 hours, and solid particles settle at the bottom of an alkaline aqueous solution containing sodium ions. Referring to operation 140, the solid in the aqueous mixture is recovered to form the zirconia nanoparticle material with the carbonate coordinated thereon. First, the solid is separated from the alkaline aqueous solution, and a washing process is applied to remove the sodium ions remained in the solid. After the sodium ions are removed, the solid is dried to obtain the zirconia nanoparticle material with the carbonate coordinated thereon. Because the zirconia nanoparticles will not aggregate, the zirconia nanoparticle material could be stored in solid form.

In embodiments, the sodium ions are removed by washing the solids with water, acetone, carbonic acid, ammonium bicarbonate, or a combination thereof.

The zirconia nanoparticle material obtained by the process has high crystallinity, and the zirconia nanoparticles are in cubic phase. The particle size of the zirconia nanoparticle is in a range from about 1 nm to 10 nm. The specific surface area is in a range from about 100 $m^2/g$ to about 250 $m^2/g$.

Moreover, the carbonate is coordinated on the surface of the zirconia nanoparticle. The carbonate is a weak ligand, which could be replaced easily by other ligand to make the zirconia nanoparticle dispersible in different solvents. For example, organic acids, organic sulfonic acid or organic phosphonic acid replaces the carbonate and coordinates on the surface of the zirconia nanoparticle. If these acids have carboxylic groups, amino groups, or alcohol groups on the alkyl chain, the zirconia nanoparticle will be dispersible in the water or an alcohol solvent. Similarly, if these acids have ester group, aromatic chain or aliphatic chain, the zirconia nanoparticle will be dispersible in an ester solvent, an aromatic solvent or an aliphatic solvent.

The following embodiments are disclosed with detailed description. For clarity, many details of practice are explained in the following descriptions. However, it should be understood that these details of practice do not intend to limit the present disclosure. Therefore, the scope of the disclosure should not be limited to the following specific examples.

Measuring equipments and methods in following embodiments are described herein. A Bruker D8 advance X-ray Diffractometer with Copper Kα X-rays are applied to measure a characteristic diffraction peak of the zirconia nanoparticle, and the Scherrer formula is applied to compute the crystal size by the full width at half maximum of the characteristic diffraction peak. However, the difference between the cubic phase and the tetragonal phase is difficult to be distinguished in the X-ray diffraction analysis, so Raman spectra are necessary to make the judgment. A BWII-UniRAM (Protrustech Co. Ltd) is applied to measure the surface enhanced Raman reflection spectra.

Further, solid-state NMR spectra (OXFORD AS500) are applied to measure the 13C CP/MAS NMR for assuring the carbonate or the carboxylate coordinated on the surface of the zirconia nanoparticle. The amount of carbonate or the carboxylate on the surface of the zirconia nanoparticle is analyzed with a Pyris-1 TGA (PerkinElmer Co. Ltd). The particle size of the zirconia nanoparticles is observed with a HR-TEM (JEOL JEM-2100).

Embodiment 1

Preparing the Zirconia Nanoparticles with Different Washing Method.

Experiment 1: Washing the Zirconia Nanoparticles with Deionized Water 200 g sodium hydroxide and 472.8 g zirconium basic carbonate (ZBC) powder are added into 127.2 g deionized water. The zirconium basic carbonate powders contain 52.6 parts by weight of hydrated water. After stirring, white slurry is obtained, which is placed in an oven at about 110° C. for 12 hours. The clear supernatant on the top is removal to recover the wet solids, which contain zirconia at about 50 parts by weight. The wet solids are flushed with the deionized water for three times. Each time it is mixed with about 3 liters of the deionized water. The settled wet solids are recovered by removing the supernatant. After the washing process, the wet solids are dried at vacuum to obtain the zirconia nanoparticles having the carbonate coordinated thereon. The zirconia nanoparticles are calcined at 100° C., 200° C., 300° C., 400° C., 500° C., 600° C. and 700° C. for 2 hours. The X-ray diffraction analysis is applied to calculate the crystal size, while the Raman spectra is taken to analyze the crystalline phase.

Figure 2:
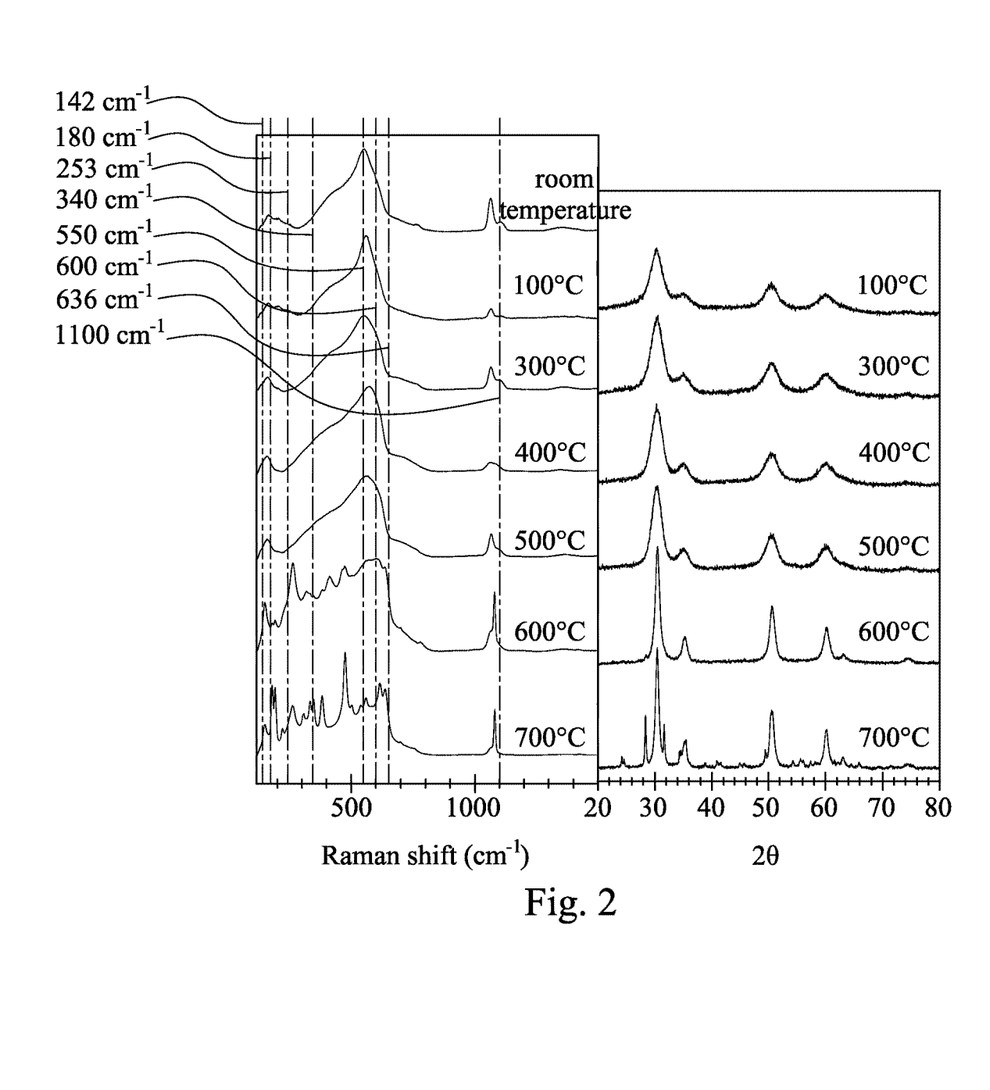
FIG. 2 is the X-ray diffraction analysis and the Raman spectra of the zirconia nanoparticles prepared in Experiment 1, in accordance with various embodiments.
Figure 3A:
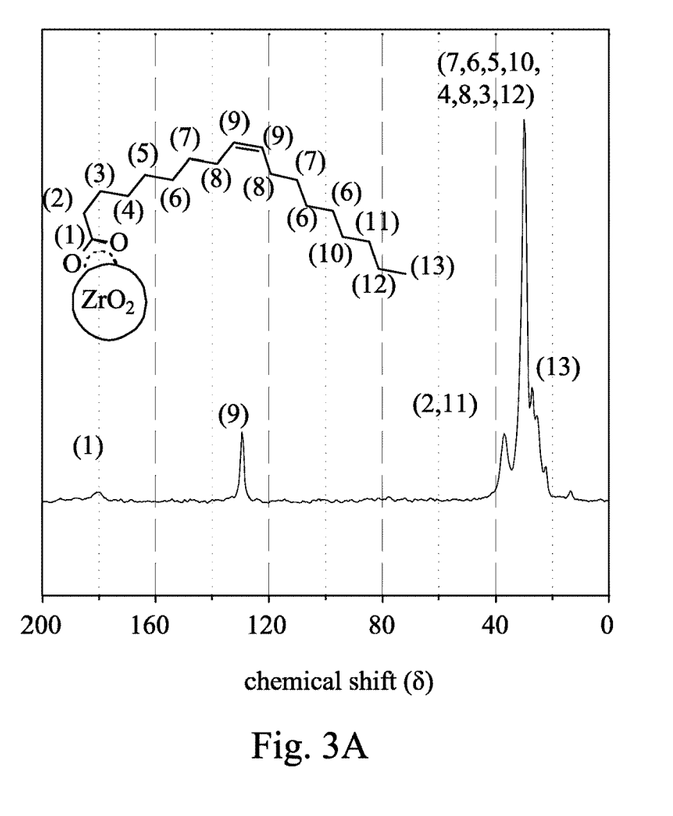
FIGS. 3A, 3B, 3C and 3D are 13C NMR of the zirconia nanoparticles having different organic acids coordinated thereon, in accordance with various embodiments.
Figure 3B:
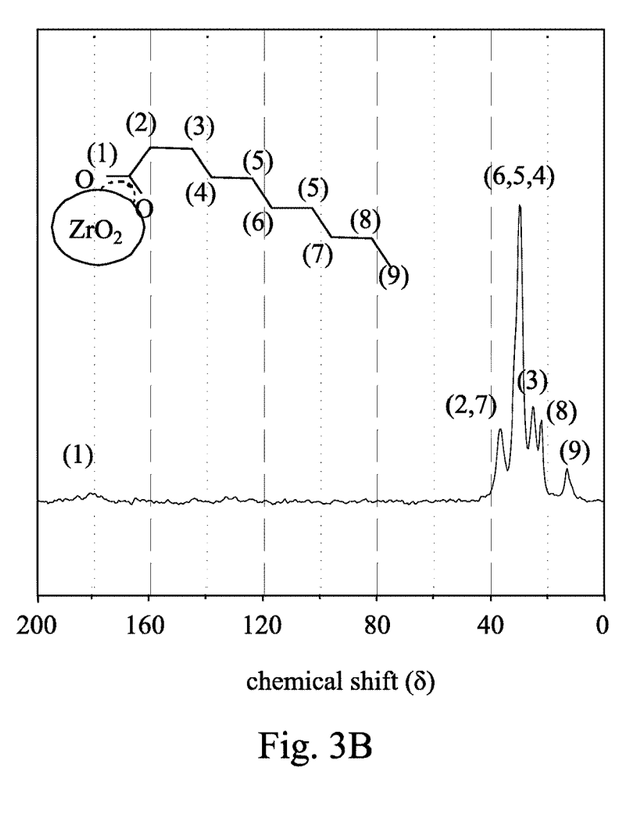
Figure 3C:
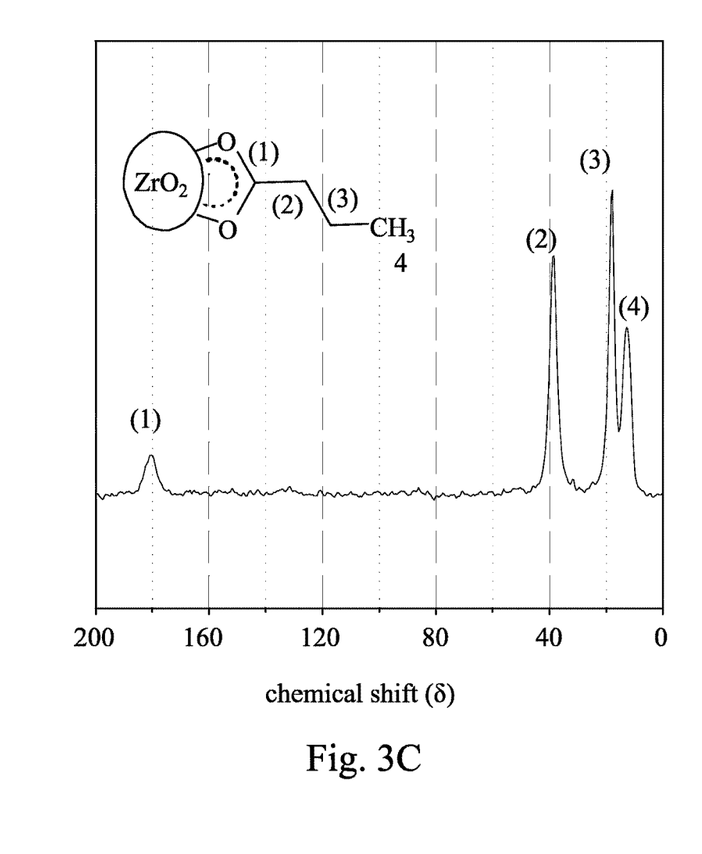
Figure 3D:
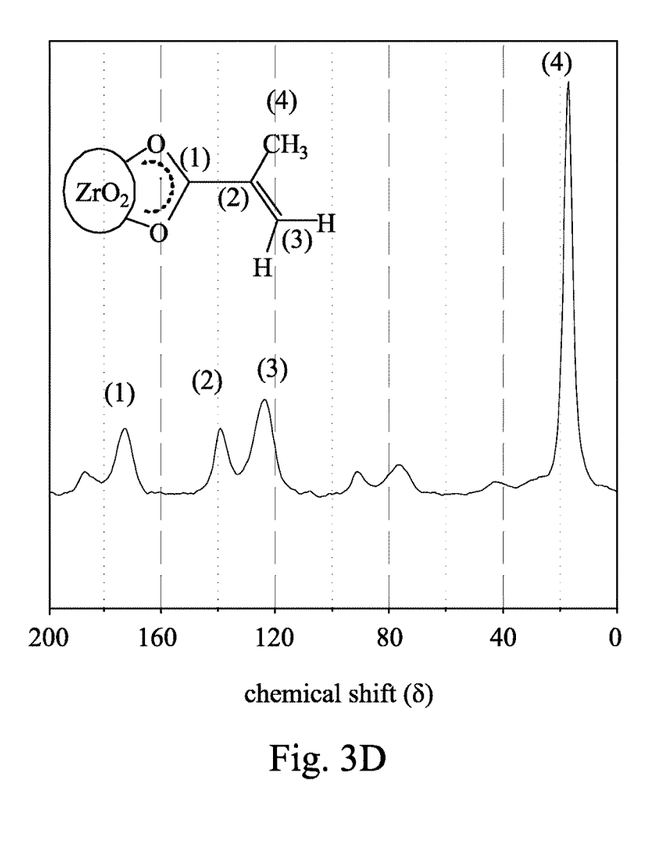

Please referring to FIG. 2, FIG. 2 is the X-ray diffraction analysis and the Raman spectra of the zirconia nanoparticles prepared in Experiment 1. The X-ray diffraction analysis is shown in right side of FIG. 2, diffraction peaks becomes more intense when calcination temperature becomes higher. It represents that the zirconia nanoparticles have better crystallinity at high temperature. As shown in the Raman spectra in left side of FIG. 2, the zirconia nanoparticles have absorption peaks at about 600 $cm^{-1}$ and at about 1100 $cm^{-1}$. The absorption peak at about 600 $cm^{-1}$ is the characteristic peak of the cubic zirconia, and the absorption peak at about 1100 $cm^{-1}$ proves that the carbonate is coordinated on the surface of the zirconia nanoparticles. As the calcination temperature increasing to 500° C., the Raman spectra of zirconia nanoparticles do not show characteristic peaks of other crystalline phase. The crystalline phase of zirconia nanoparticles is pure cubic phase.

When increasing the calcination temperature to 600° C., the Raman spectra of zirconia nanoparticles has absorption peaks at about 142 $cm^{-1}$, 253 $cm^{-1}$ and 636 $cm^{-1}$. These absorption peaks are characteristic peaks of the tetragonal zirconia, and the zirconia nanoparticles are not in pure cubic phase anymore. The crystalline phase of the zirconia nanoparticles is a mixed phase of cubic phase and tetragonal phase after 600° C. heating. When increasing the heating temperature to 700° C., the Raman spectra of zirconia nanoparticles has double absorption peaks at about 180 $cm^{-1}$, 340 $cm^{-1}$ and 550 $cm^{-1}$. These double absorption peaks are characteristic peaks of the monoclinic zirconia, and the crystalline phase of zirconia nanoparticles is now a mixed phase of cubic phase, monoclinic phase and tetragonal phase after 700° C. calcination.

Experiment 2: Washing the Zirconia Nanoparticles with Deionized Water and Acetone Preparing the wet solids as the same way in Experiment 1, and the zirconia is 50 parts by weight of the wet solids. The wet solids are flushed with the deionized water for three times. Each time the wet solids are mixed with about 3 liters of the deionized water, and the deionized water is removal after the powder settled. Further, water between the zirconia nanoparticles is replaced with acetone. After the washing process, the wet solids are dried at vacuum at about 100° C. to obtain the zirconia nanoparticles having the carbonate coordinated thereon.

Experiment 3: Washing the Zirconia Nanoparticles with Deionized Water and Ammonium Bicarbonate Solution Preparing the wet solids as the same way in Experiment 1, and the zirconia is 50 parts by weight of the wet solids. First, the wet solids are flushed with the ammonium bicarbonate solution, and a molar concentration of the ammonium bicarbonate solution is 2 M. Then, the wet solids are flushed with the deionized water. After the washing process, the wet solids are dried at vacuum at about 100° C. to obtain the zirconia nanoparticles having the carbonate coordinated thereon.

The zirconia nanoparticles prepared by Experiment 1, 2 and 3 are calcined at 100° C., 200° C., 300° C., 400° C., 500° C., 600° C. and 700° C. for 2 hours. The X-ray diffraction analysis is applied to calculate the crystal size, while the Raman spectra are taken to analyze the crystalline phase. The experimental results are shown in Table 1.

TABLE 1

The crystalline phases and particle sizes of the zirconia nanoparticles prepared in Embodiment 1.

| calcination temperature (° C.) | Experiment 1 crystalline phase | size (nm) | Experiment 2 crystalline phase | size (nm) | Experiment 3 crystalline phase | size (nm) |
| --- | --- | --- | --- | --- | --- | --- |
| room | C | 3.2 | C | 3.2 | C | 3.2 |
| 100 | C | 3.4 | C | 3.2 | C | 3.2 |
| 300 | C | 3.6 | C | 3.4 | C | 3.6 |
| 400 | C | 3.7 | C | 3.7 | T | 6.0 |
| 500 | C | 4.3 | C + T | 7.9 | T | 6.8 |
| 600 | C + T | 9.5 | C + T + M | 11.9 | T | 9.1 |

In Table 1, C is cubic phase, T is tetragonal phase and M is monoclinic phase. As shown in Table 1, the zirconia nanoparticles prepared with different washing methods are in pure cubic phase at room temperature. Further, the particle sizes are about 3.2 nm, so the zirconia nanoparticles will have high specific surface area. But washing method will influence the crystalline phase of the zirconia nanoparticles after calcination. Washing the zirconia nanoparticles with deionized water could not remove residual sodium ions completely. If washing with oxygenated solvents, e.g., the acetone, which will partially replace the carbonate on the surface of the zirconia nanoparticles and influence the crystalline phase. In Table. 1, the zirconia nanoparticles in Experiment 2 are in the mixed phase of cubic phase and tetragonal phase after 500° C. calcination. Comparatively, the zirconia nanoparticles in Experiment 1 are still in pure cubic phase after 500° C. calcination.

Experiment 3 uses the ammonium bicarbonate solution to replace and remove the sodium ions. The zirconia nanoparticles in Experiment 3 showed phase transition after 400° C. calcination, and the crystalline phase of the zirconia nanoparticles transfers from pure cubic phase to pure tetragonal phase. The crystallinity of the zirconia nanoparticles is enhanced at high temperature, and the particle sizes of the zirconia nanoparticles also become larger. Obviously, the zirconia nanoparticles are not monomodal distributed in size at high temperature. Since the zirconia nanoparticles will aggregate and phase transform at high temperature, the heating temperature should not exceed 300° C. to obtain zirconia nanoparticles in pure cubic phase.

In embodiments, the temperature of preparing the zirconia nanoparticles is controlled in a range from about 90° C. to 300° C., better in a range from about 90° C. to 120° C.

Embodiment 2

Changing the Weight of Deionized Water and the Sodium Hydroxide to Prepare the Zirconia Nanoparticles.

The precursor includes 472.8 g zirconium basic carbonate (ZBC) powder, and the weight of the deionized water and the weight of the sodium hydroxide are shown in Table 2. After heating the aqueous mixture at 110° C. for about 12 hours, the wet solids are flushed with deionized water for three times as the same way in Experiment 2. Each time the wet solids are mixed with about 3 liters of the deionized water, and the settling wet solids are recovered by removing the supernatant. Further, water between the zirconia nanoparticles is replaced with the acetone. After the washing process, the wet solids are dried at vacuum at about 100° C. to obtain the zirconia nanoparticles having the carbonate coordinated thereon. The X-ray diffraction analysis is applied to calculate the crystal size, while the Raman spectra are taken to analyze the crystalline phase. The experimental results are shown in Table 3.

TABLE 2

Compositions of the precursors in Embodiment 2.

| | ZBC (g) | sodium hydroxide (g) | deionized water (g) | Zr (%) | Na (%) | Na(mol)/ carbonate (mol) |
| --- | --- | --- | --- | --- | --- | --- |
| Experiment 2 | 472.8 | 200 | 127.2 | 18.5 | 14.4 | 9.1 |
| Experiment 4 | 472.8 | 160 | 167.2 | 18.5 | 11.5 | 7.3 |
| Experiment 5 | 472.8 | 120 | 207.2 | 18.5 | 8.6 | 5.5 |
| Experiment 6 | 472.8 | 80 | 247.2 | 18.5 | 5.8 | 3.7 |
| Experiment 7 | 472.8 | 64 | 263.2 | 18.5 | 4.6 | 2.9 |
| Experiment 8 | 472.8 | 56 | 271.2 | 18.5 | 4.0 | 2.6 |
| Experiment 9 | 472.8 | 48 | 279.2 | 18.5 | 3.5 | 2.2 |
| Experiment 10 | 472.8 | 40 | 287.2 | 18.5 | 2.9 | 1.8 |

TABLE 3

The crystalline phases and particle sizes of the zirconia nanoparticles prepared in Embodiment 2.

| | crystalline phase | cubic phase ratio (%) | size (nm) |
| --- | --- | --- | --- |
| Experiment 2 | C | 100 | 3.2 |
| Experiment 4 | C | 100 | 3.6 |
| Experiment 5 | C | 100 | 4.8 |
| Experiment 6 | C | 100 | 6.9 |
| Experiment 7 | C | 100 | 7.8 |
| Experiment 8 | C + M | 87 | 7.2 |
| Experiment 9 | C + M | 82 | 6.1 |
| Experiment 10 | C + M | 77 | 4.5 |

In Table. 2, Experiment 2 and Experiment 4-10 change the weights of the deionized water and the sodium hydroxide in the precursor, but total weight of the aqueous mixture is fixed. More specifically, when the weight of the sodium hydroxide is decreased, the weight of the deionized water is increased to balance the total weight. Thus, a molar ratio of sodium to the carbonate is decreased. Please refer to Table 3 and Table 2 at the same time. When the molar ratio is over than 2.6, the zirconia nanoparticles are in pure cubic phase. But when the molar ratio decreasing to about 2.6, e.g., Experiment 8, the zirconia nanoparticles are not in pure cubic phase anymore, and some zirconia nanoparticles are in monoclinic phase. As the molar ratio continues decreasing, a ratio of the monoclinic phase in the zirconia nanoparticles is increased. Therefore, the molar ratio of the sodium to the carbonate will influence the crystalline phase of the zirconia nanoparticles, and the molar ratio should not be less than 2.6 to assure the crystalline phase of the zirconia nanoparticles is pure cubic phase.

Embodiment 3

Changing the Heating Time to Prepare the Zirconia Nanoparticles.

32 g sodium hydroxide and 227 g zirconium basic carbonate (ZBC) powder are added into 140.7 g deionized water. After stirring, white aqueous slurry is obtained. The zirconium is 17.8 parts by weight of the aqueous slurry, and the sodium is 4.6 parts by weight of the aqueous slurry. The molar ratio of the sodium to the carbonate is 3.0. The precursor is heated at about 110° C., and the heating time is 6, 12, 24, 36 and 48 hours. After heating, the wet solids are flushed with deionized water for three times. Each time the wet solids are mixed with about 3 liters of the deionized water, and the settled wet solids are recovered by removing the supernatant. Further, water between the zirconia nanoparticles is replaced with acetone. After the washing process, the wet solids are dried at vacuum at about 100° C. to obtain the zirconia nanoparticles having the carbonate coordinated thereon. The X-ray diffraction analysis is applied to calculate the crystal size, while the Raman spectra are taken to analyze the crystalline phase. The experimental results are shown in Table 4.

TABLE 4

The crystalline phases and particle sizes of the zirconia nanoparticles prepared in Embodiment 4 by changing the heating time.

| Heating time (hr) | crystalline phase | cubic phase ratio (%) | size (nm) |
|---|---|---|---|
| 6 | C | 100 | 7.9 |
| 12 | C | 100 | 8.0 |
| 24 | C | 100 | 8.1 |
| 36 | C + M | 90 | 7.8 |
| 48 | C + M | 88 | 7.6 |

As shown in Table. 4, heating time will influence the crystalline phase of the zirconia nanoparticles. Although the sodium-to-carbonate molar ratio is 3.0, which is larger than 2.6, some zirconia nanoparticles are in monoclinic phase when the heating time is over 24 hours. As the heating time continues increasing, the ratio of the monoclinic phase in the zirconia nanoparticles is increased. Therefore, the heating time will influence the crystalline phase of the zirconia nanoparticles, and the heating time should be controlled in a range from about 3 to 24 hours to assure the crystalline phase of the zirconia nanoparticles is pure cubic phase.

In embodiments, the heating time is in a range from about 4 to 12 hours.

Embodiment 4

Preparing the Zirconia Nanoparticles with Zirconium Hydroxide.

Hydrous Zirconium Hydroxide is Prepared First. 104.6 g Zirconium oxychloride is dissolved in 50 g deionized water, and then stirred to obtain a light-yellowish transparent solution. Further, 30 g sodium hydroxide solution is prepared, and a weight percent of the sodium hydroxide solution is 33.07. The sodium hydroxide solution is added to the zirconium oxychloride solution, and a suspension of zirconium hydroxide is obtained. A pH value of the suspension is 7.4. The zirconium hydroxide in the suspension is centrifuged and washed with deionized water for three times to obtain 191 g hydrous zirconium hydroxide. The hydrous zirconium hydroxide includes 51.68 g zirconium hydroxide, 1.52 g sodium chloride and 137.8 g water. The hydrous zirconium hydroxide is divided into 4 parts. Sodium hydroxide, sodium carbonate and deionized water with the weight shown in Table 5 are added into the hydrous zirconium hydroxide to prepare a precursor. The precursor is heated at 110° C. for about 12 hours. After heating, the wet solids are flushed centrifugally with the ammonium bicarbonate solution for three times, and further flushed with deionized water for one time. The wet solids are dried at vacuum at about 100° C. to obtain the zirconia nanoparticles having the carbonate coordinated thereon. The X-ray diffraction analysis is applied to calculate the crystal size, while the Raman spectra are taken to analyze the crystalline phase. The experimental results are shown in Table 6.

TABLE 5

Compositions of the precursors in Embodiment 4.

| | zirconium hydroxide (g) | sodium hydroxide (g) | deionized water (g) | sodium carbonate (g) | sodium chloride (g) | Na(mol)/ carbonate (mol) |
|---|---|---|---|---|---|---|
| Experiment 11 | 12.92 | 8.9 | 39.3 | 4.75 | 0.38 | 7.11 |
| Experiment 12 | 12.92 | 7.5 | 38.9 | 6.6 | 0.38 | 5.12 |
| Experiment 13 | 12.92 | 4.95 | 38.0 | 10.0 | 0.38 | 3.38 |
| Experiment 14 | 12.92 | 2.7 | 37.3 | 13.0 | 0.38 | 2.6 |

TABLE 6

The crystalline phases and particle sizes of the zirconia nanoparticles prepared in Embodiment 4.

| | crystalline phase | cubic phase ratio (%) | size (nm) |
|---|---|---|---|
| Experiment 11 | C | 100 | 3.2 |
| Experiment 12 | C | 100 | 3.7 |
| Experiment 13 | C | 100 | 4.0 |
| Experiment 14 | C | 100 | 5.1 |

As shown in Table. 6, the molar ratio of the sodium to the carbonate is no less than 2.6, and the heating time is not over than 24 hours. Thus, preparing the zirconia nanoparticles with zirconium hydroxide could also obtain the zirconia nanoparticles, and the crystalline phase of the zirconia nanoparticles is pure cubic phase. The dispersivity of the zirconia nanoparticles is well, and the particle sizes are in a range from about 3.2 nm to 5.1 nm, so the zirconia nanoparticles will have high specific surface area.

Embodiment 5

Preparing Zirconia Nanoparticles with Zirconium Carbonate and Potassium Hydroxide.

Preparing the zirconia nanoparticles as the same way in Experiment 2. The zirconium basic carbonate (ZBC) powder employed is freshly unpacking and contains 47 parts by weight of hydrated water. Further, the sodium hydroxide in the precursor is replaced with potassium hydroxide, and the weight of the zirconium carbonate, potassium hydroxide and the deionized water are shown in Table. 7. The wet solids are flushed with the deionized water for three times as the same way in Experiment 2. Each time the wet solids are mixed with about 3 liters of the deionized water, and the settled wet solids are recovered by removing the supernatant. Further, water between the zirconia nanoparticles is replaced with the acetone. After the washing process, the wet solids are dried at vacuum at about 100° C. to obtain the zirconia nanoparticles having the carbonate coordinated thereon. The X-ray diffraction analysis is applied to calculate the crystal size, while the Raman spectra are taken to analyze the crystalline phase. The experimental results are shown in Table 8.

TABLE 7

Compositions of the precursors in Embodiment 5.

| | zirconium carbonate (g) | potassium hydroxide (g) | deionized water (g) | Zr (%) | K (%) | K(mol)/carbonate (mol) |
|---|---|---|---|---|---|---|
| Experiment 15 | 848 | 400 | 352 | 18.5 | 17.4 | 6.4 |
| Experiment 16 | 636 | 240 | 324 | 18.5 | 13.9 | 5.1 |
| Experiment 17 | 636 | 180 | 384 | 18.5 | 10.5 | 3.8 |
| Experiment 18 | 636 | 120 | 444 | 18.5 | 7.0 | 2.6 |
| Experiment 19 | 636 | 96 | 468 | 18.5 | 5.6 | 2.0 |

TABLE 8

The crystalline phases and particle sizes of the zirconia nanoparticles prepared in Embodiment 5.

| | crystalline phase | cubic phase ratio (%) | size (nm) |
|---|---|---|---|
| Experiment 15 | C + M | 89 | 4.0 |
| Experiment 16 | C + M | 86 | 4.6 |
| Experiment 17 | C + M | 85 | 5.8 |
| Experiment 18 | C + M | 74 | 6.5 |
| Experiment 19 | C + M | 69 | 5.4 |

As shown in Table. 8, the zirconia nanoparticles could be prepared with zirconium carbonate and potassium hydroxide, and the crystalline phase of the zirconia nanoparticles is the mixed phase of cubic phase and monoclinic phase. As the molar ratio of the potassium to the carbonate decreases, the weight ratio of the monoclinic phase in the zirconia nanoparticles increased. In Experiment 19, the molar ratio of the potassium to the carbonate is 2.0, and thus the weight ratio of the cubic phase in the zirconia nanoparticles also decreases to about 69%. Preparing the zirconia nanoparticles with zirconium carbonate and potassium hydroxide will obtain the zirconia nanoparticles having cubic phase and monoclinic phase. Besides, the dispersivity of the zirconia nanoparticles is well, and the particle sizes are in a range from about 4 nm to 6.5 nm, so the zirconia nanoparticles have high specific surface area.

Embodiment 6

Replacing the Carbonate on the Surface of the Zirconia Nanoparticles with the Organic Acids, and the Zirconia Nanoparticles are Dispersed in Different Solvents.

As aforementioned, the zirconia nanoparticles prepared in embodiments have the carbonate coordinated thereon. Because the carbonate is a weak ligand, other ligand will replace the carbonate and coordinate on the surface of the zirconia nanoparticles. The exchanged ligand contains functional groups making zirconia nanoparticles disperse in different solvents.

Add the zirconia nanoparticles prepared in Experiment 3 into different organic acid solutions, e.g., an alcoholic solution containing oleic acid or decanoic acid, or an aqueous solution of butanoic acid or methacrylic acid. These organic acids will replace the carbonate on the surface of the zirconia nanoparticles, and the carbonate will turn into carbon dioxide and form plurality of tiny bubbles. The mixtures are stirred at 60° C. for 2 hours, and solids in the mixtures are separated centrifugally. The solids are flushed with water (oleic acid and decanoic acid are flushed with alcohol) for a few times. The solids are dried at vacuum at about 80° C. to obtain the zirconia nanoparticles having the organic acid coordinated thereon. The 13C NMR of the zirconia nanoparticles is measured to assure the organic acid is coordinated on the surface of the zirconia nanoparticles. Please refer to FIGS. 3A, 3B, 3C and 3D. FIGS. 3A, 3B, 3C and 3D are 13C NMR of the zirconia nanoparticles having different organic acids coordinated thereon. The organic acid coordinated on the zirconia nanoparticles in FIGS. 3A, 3B, 3C and 3D are oleic acid, decanoic acid, butanoic acid and methacrylic acid, respectively. As shown in FIGS. 3A, 3B, 3C and 3D, the 13C NMR characteristic peaks of these organic acids are measured, relatively. The 13C NMR characteristic peaks of the carbonate are not found. It assures that these organic acids replace the carbonate and coordinate on the surface of the zirconia nanoparticles.

Figure 4:
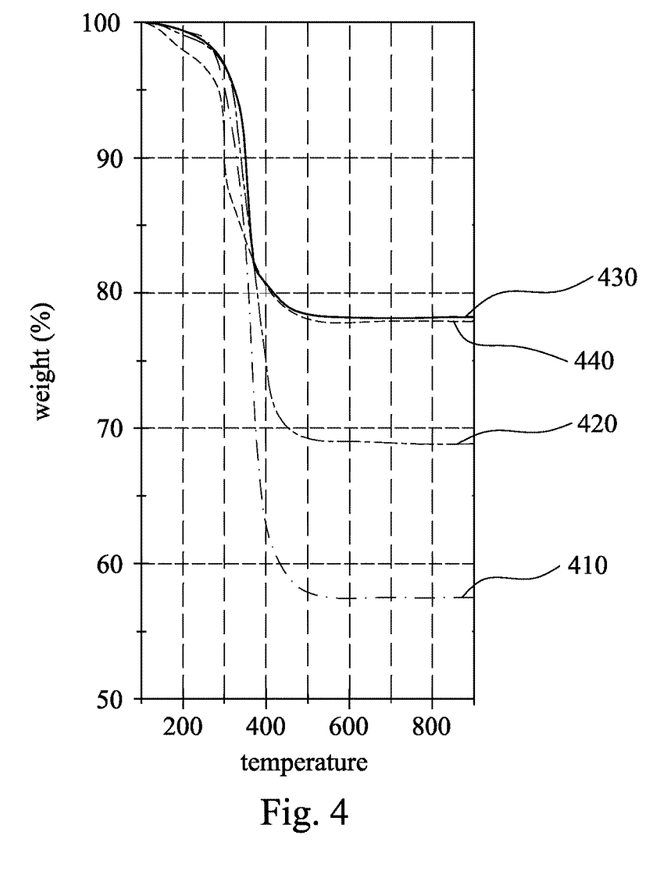
FIG. 4 is a graph of thermal gravitational analysis of zirconia nanoparticles having different organic acids coordinated thereon, in accordance with various embodiments.

A thermal gravitational analyzer is applied to measure the weight of the organic acid on the zirconia nanoparticles. Please referring to FIG. 4, FIG. 4 is a graph of thermal gravitational analysis of zirconia nanoparticles having different organic acids coordinated thereon. The organic acid coordinated on the zirconia nanoparticles in Experiment 410, 420, 430 and 440 is oleic acid, decanoic acid, butanoic acid and methacrylic acid, respectively. When increasing temperature, the organic acid on the surface of the zirconia nanoparticles is oxidized to decrease a total weight. As the total weight stops decreasing, the organic acid is completely oxidized, and the zirconia nanoparticles without the coordinating ligand thereon are left. Please refer to experiment 410, since the weight is no longer decreasing, the residual weight is only 57.5 parts by weight of the total weight before heating. It could be calculated that the oleic acid coordinated on the surface of the zirconia nanoparticles is 42.5 parts by weight of the total weight before heating. As the same reason, the decanoic acid, butanoic acid and methacrylic acid are 31.2, 21.8 and 22.1 parts by weight of the total weight before heating. Thus, these organic acids could replace the carbonate easily, and the weight of the organic acids on the zirconia nanoparticles is much higher than the carbonate.

Experiment 410, 420, 430 and 440 are dispersed in different solvents to analyze the dispersity. The results are shown in Table 9.

TABLE 9

Dispersity of the zirconia nanoparticles having different organic acids coordinated thereon.

| solvent | ligand | | | |
|---|---|---|---|---|
| | oleic acid, | decanoic acid | butanoic acid | methacrylic acid |
| hexane | ○ | ○ | X | X |
| cyclohexane | ○ | ○ | ○ | X |
| ethylbenzene | ○ | ○ | ○ | X |
| benzene | ○ | ○ | ○ | ○ |
| Toluene | ○ | ○ | ○ | ○ |
| m-xylene | ○ | ○ | ○ | X |
| o-xylene | ○ | ○ | ○ | ○ |
| p-xylene | ○ | ○ | ○ | X |
| styrene | ○ | ○ | ○ | X |
| methacrylic | X | X | X | ○ |
| chloroform | ○ | ○ | ○ | ○ |
| butyl acetates | ○ | X | X | X |
| tetrahydrofuran | ○ | ○ | ○ | ○ |

The [○] symbol represents that the zirconia nanoparticles will disperse in the solvent transparently. The [X] symbol represents that the zirconia nanoparticles do not disperse in the solvent but settle at the bottom of the solvent. As shown in Table 9, the carbonate coordinated on the surface of the zirconia nanoparticles is replaced with different organic acids, and thus the zirconia nanoparticles could be dispersed in a suitable solvent. Further, the carbonate is replaced with different organic acids directly and turns into the carbon dioxide to dissipate in the air. Therefore, a secondary process of removing the carbonate from the zirconia nanoparticles is not necessary, which improves the efficiency of the process significantly.

Figure 5:
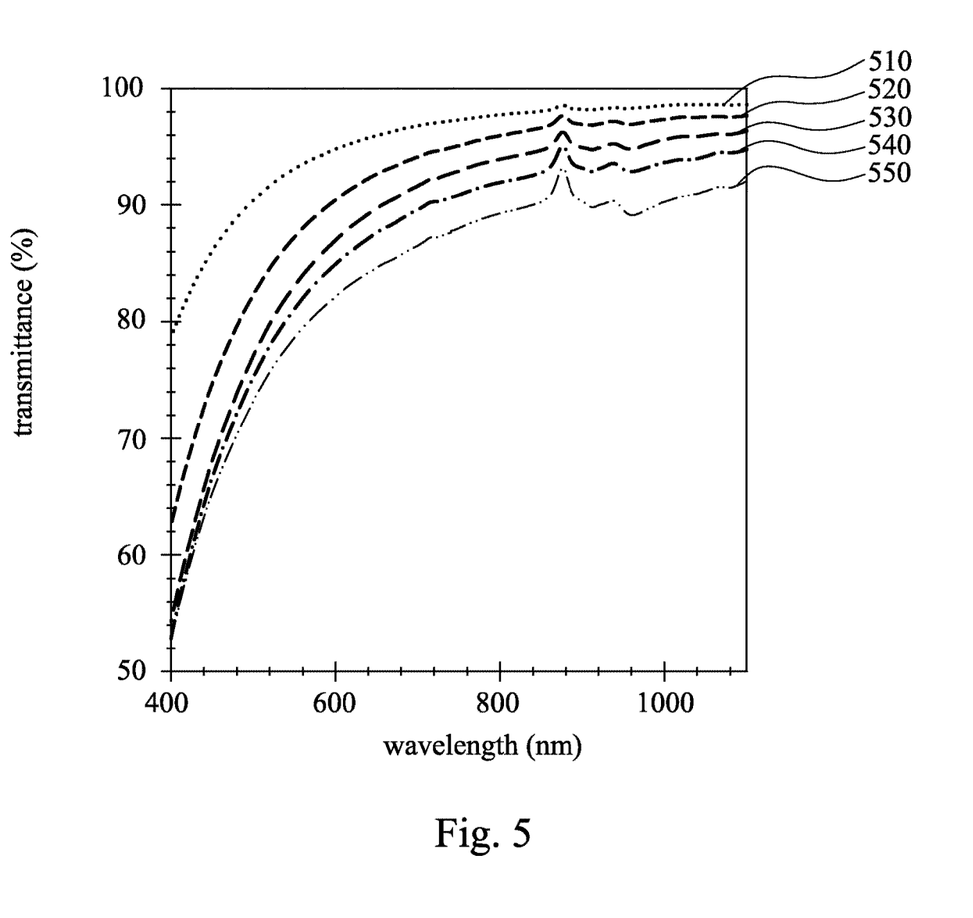
FIG. 5 illustrates a transmittance of the toluene when dispersing the zirconia nanoparticles having the butanoic acid coordinated thereon in the toluene, in accordance with various embodiments.

Please refer to FIG. 5, FIG. 5 illustrates the transmittance of the toluene when dispersing the zirconia nanoparticles having the butanoic acid coordinated thereon in the toluene. The zirconia nanoparticles are added at different parts by weight of the dispersion. The zirconia nanoparticles are 10, 20, 30, 40 and 50 parts by weight of the dispersion in Experiment 510, 520, 530, 540 and 550, respectively. In FIG. 5, since the transmittance of these dispersions are all over 50%, which the excellent transparency could be observed visually. It could be inferred that organic acids or suitable functional groups will replace the carbonate easily and make the zirconia nanoparticles disperse in different solvents.

Embodiment 7

Preparing the Zirconia Nanoparticles Doped with Calcium Ions.

As aforementioned, the zirconia nanoparticles are transformed from the pure cubic phase to mixed phase at high temperature. Thus, the heating temperature should be controlled at about 90° C. to 120° C. If doping with an element of calcium, magnesium, yttrium, titanium, aluminum, cerium, lanthanide or a combination thereof in the zirconia nanoparticles during preparation, the phase stability of the zirconia nanoparticles could be enhanced. The zirconia nanoparticles will prevent from phase transition after high temperature treatment.

19.5 g sodium hydroxide, 15.14 g deionized water and 42.35 g zirconium basic carbonate (ZBC) powder are mixed to obtain a white aqueous mixture. Further, 3.01 g calcium hydroxide is added to the white aqueous mixture and stir to obtain slurry, which is heated at 110° C. for about 6 hours. After heating, the slurry is cooled down to the room temperature, and the upper cloudy liquid is removal. The remained solids are flushed with deionized water for two times. Each time the solids are mixed with about 200 g of the deionized water, and the wet solids are separated centrifugally.

A half of the wet solids are flushed with 200 g deionized water. Because the pH value of the wet solids is too high, 2.4 g hydrogen chloride is further added to adjust the pH value to about 7. When the solids are settling, the clear supernatant on the top is removal to recover solids. The solids are flushed with deionized water by the method mentioned above. The solids are dried at vacuum at 40° C. to obtain the zirconia nanoparticles doped with calcium ions, with the carbonate coordinated on the surface of the zirconia nanoparticles. The zirconia nanoparticles are calcined in a tubular furnace, and the temperature is increased from room temperature to 1400° C. at a rate of 10° C./min. After maintaining the zirconia nanoparticles at 1400° C. for 2 hours, the zirconia nanoparticles are cooled down to the room temperature naturally. The X-ray diffraction analysis is applied to calculate the crystal size, while the Raman spectra are taken to analyze the crystalline phase.

Figure 6:
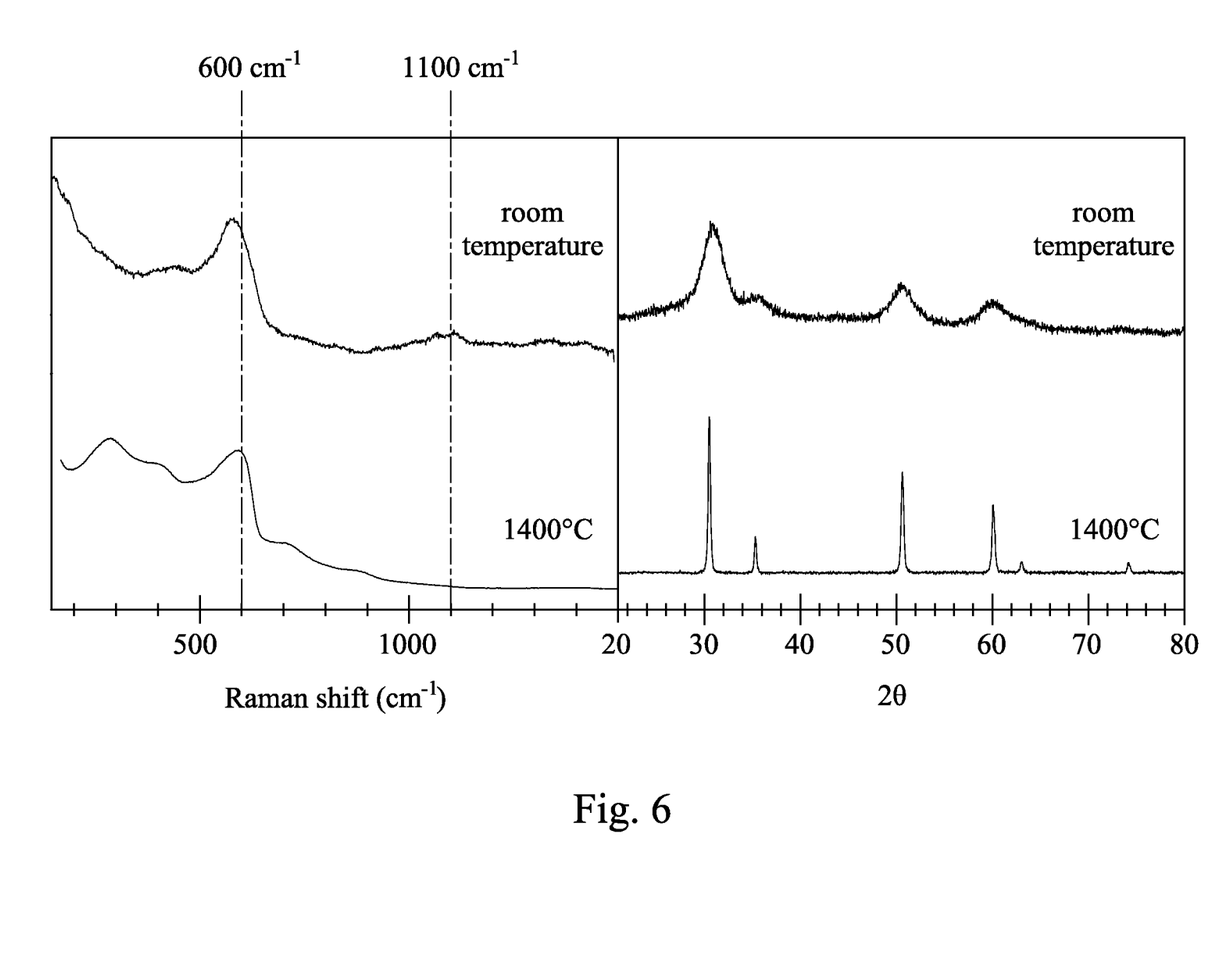
FIG. 6 is the X-ray diffraction analysis and the Raman spectra of the zirconia nanoparticles prepared in Embodiment 7, in accordance with various embodiments.

Please refer to FIG. 6, FIG. 6 is the X-ray diffraction analysis and the Raman spectra of the zirconia nanoparticles in Embodiment 7, in which the zirconia nanoparticles are doped with calcium ions, and the carbonate is coordinated on the surface of the zirconia nanoparticles. As shown in the X-ray diffraction analysis of FIG. 6, when the calcination temperature increased to 1400° C., the diffraction peaks of the zirconia nanoparticles become more intense. Thus, the zirconia nanoparticles will have higher crystallinity after high temperature treatment. Continuing to the Raman spectra of FIG. 6. The Raman spectra of zirconia nanoparticles do not show characteristic peaks of monoclinic phase or tetragonal phase before or after calcination, and the zirconia nanoparticles are in pure cubic phase. When calcination temperature increased to 1400° C., the carbonate coordinated on the surface of the zirconia nanoparticle is removed, thus, the adsorption peak at about 1100 $cm^{-1}$ also disappears. Because the zirconia nanoparticles are not protected by the carbonate anymore, the particles will aggregate to increase the particle sizes from 3.6 nm to 42.6 nm, and the zirconia nanoparticles are not monomodal distributed in size. Thus, calcium ion increases stability of the zirconia nanoparticles and assures the crystalline phase of the zirconia nanoparticles being pure cubic phase after high temperature calcination.

Again, organic acids could replace the carbonate and coordinate on the surface of the zirconia nanoparticles doped with calcium ions. For example, the other half of the wet solids is mixed with 37.5 g methacrylic acid solution, in which the weight percent of the methacrylic acid is 34.2. The pH value of the mixture is 4.1. After stirring the mixture at 65° C. for 4 hours, the mixture is centrifuged, and the supernatant on the top is removal. The sediment is flushed with 70 g deionized water for two times, and then the sediment is dried at vacuum at 80° C. for 8 hours to obtain the zirconia nanoparticles having the methacrylic acid coordinated thereon. The zirconia nanoparticles are doped with calcium ions to increase the stability, and phase transition will not occur at high temperature. Also, the methacrylic acid replaces the carbonate and coordinates on the surface of the zirconia nanoparticles. The methacrylic acid makes the zirconia nanoparticles disperse in chloroform or toluene to form the transparent dispersion.

Embodiment 8

Preparing the Zirconia Nanoparticles Doped with Yttrium Ions.

Preparing hydrous zirconium hydroxide including yttrium ions at first. 52.4 g zirconium oxychloride is dissolved in 25 g deionized water, and then stirring to obtain a light-yellowish transparent solution. Add 15.57 g yttrium nitrate hexahydrate into the light-yellowish transparent solution and keep stirring. After stirring, aqueous solution containing 33.07% by weight of sodium hydroxide was added and a white and pulpy product is obtained, which has a pH value of 11.63. The solids in the product are centrifuged and cleaned with deionized water for three times to obtain 104 g hydrous zirconium hydroxide including yttrium ions.

25.85 g sodium carbonate powders and 25 g deionized water are added into the hydrous zirconium hydroxide including yttrium ions for preparing the zirconia nanoparticles. After stirring, a pulpy aqueous mixture is obtained. After heating at 110° C. for about 6 hours, the pulpy aqueous mixture is cooled down to the room temperature, and the supernatant is removal. The remained solids are flushed with deionized water for three times. Each time the solids are mixed with about 200 g deionized water, and the supernatant is removal to obtain 58 g wet solids.

A half of the wet solids are added into 200 g deionized water, and the 3.9 g hydrogen chloride is added to adjust the pH value to about 7. The clear supernatant on the top is removal to recover wet solids. The wet solids are flushed with 200 g deionized water and then being centrifuged for three times. The solids are dried at vacuum at 40° C. to obtain the zirconia nanoparticles doped with yttrium ions, with the carbonate coordinated on the surface of the zirconia nanoparticles. The zirconia nanoparticles are calcined in a tubular furnace, where the temperature is increased from room temperature to 1400° C. at a rate of 10° C./min. After maintaining at 1400° C. for 2 hours, the zirconia nanoparticles is cooled down to the room temperature naturally. The X-ray diffraction analysis is applied to calculate the crystal size, while the Raman spectra are taken to analyze the crystalline phase.

Figure 7:
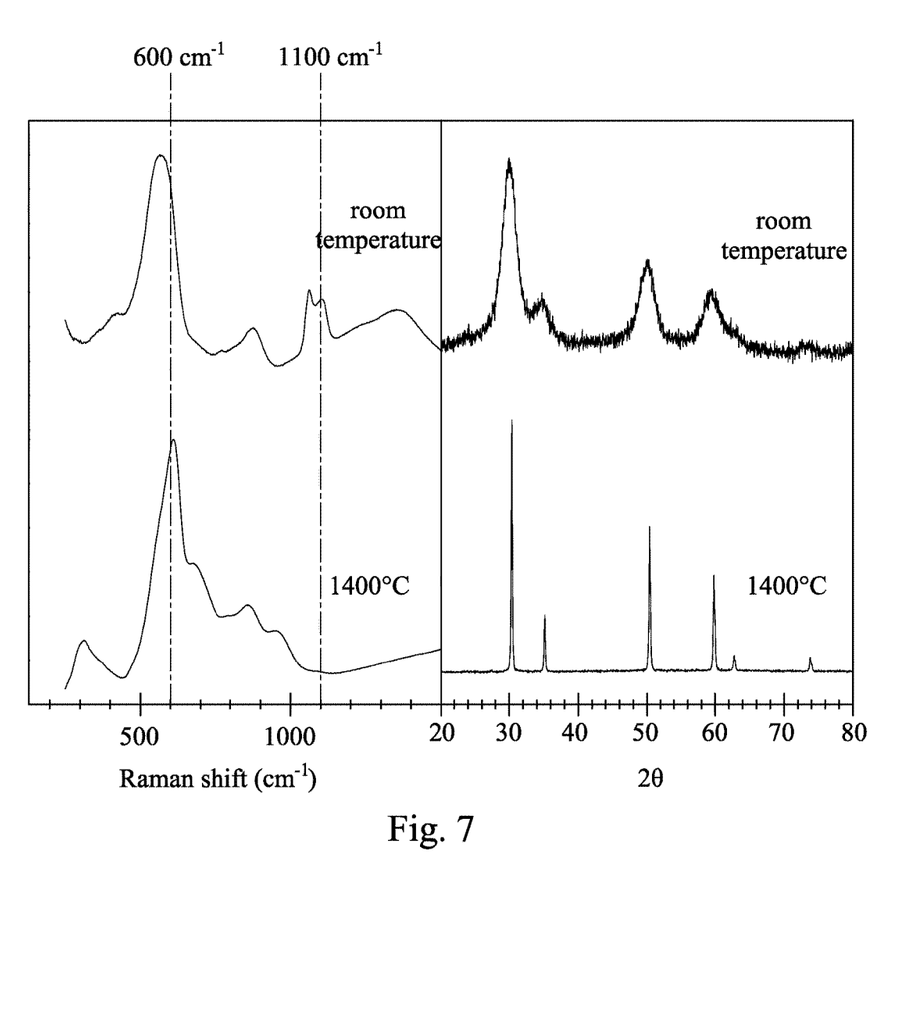
FIG. 7 is the X-ray diffraction analysis and the Raman spectra of the zirconia nanoparticles prepared in Embodiment 8, in accordance with various embodiments.

Please refer to FIG. 7, FIG. 7 is the X-ray diffraction analysis and the Raman spectra of the zirconia nanoparticles in Embodiment 8, in which the zirconia nanoparticles are doped with yttrium ion, and the carbonate is coordinated on the surface of the zirconia nanoparticles. Same as in Embodiment 7, yttrium ions also increase the phase stability of the zirconia nanoparticles and assure the crystalline phase of the zirconia nanoparticles being pure cubic phase after high temperature calcination. Also, when calcination temperature increased to 1400° C., the carbonate coordinated on the surface of the zirconia nanoparticle is removed, and the adsorption peak at about 1100 $cm^{-1}$ also disappears. Because the zirconia nanoparticles are not protected by the carbonate anymore, the particles will aggregate to increase the particle sizes from 2.4 nm to 32.7 nm. The zirconia nanoparticles are not mono-distributed in size anymore.

Similarly, organic acids could replace the carbonate and coordinate on the surface of the zirconia nanoparticles doped with yttrium ions. The remained 29 g wet solids are mixed with 37.5 g methacrylic acid solution, in which a weight percent of the methacrylic acid is 34.2. After stirring the mixture at 65° C. for 4 hours, the mixture is centrifuged, and the micro-bubble generated is carbon dioxide. The sediment is flushed with 70 g deionized water for two times, and then the sediment is dried at vacuum at 80° C. for 8 hours to obtain the zirconia nanoparticles having methacrylic acid coordinated thereon. The zirconia nanoparticles are doped with yttrium ions to increase the phase stability, and phase transition will not occur after high temperature treatment. Also, the methacrylic acid replaces the carbonate and coordinates on the surface of the zirconia nanoparticles. The methacrylic acid makes the zirconia nanoparticles disperse in chloroform or toluene to form the transparent dispersion.

The embodiments of the present disclosure discussed above have advantages over existing structures and methods, and the advantages are summarized below. Complicate operations are not necessary to replace the carbonate coordinated on the surface of the zirconia nanoparticles with another ligand, and the zirconia nanoparticles will disperse in suitable solvents. The carbonate will not remain in the dispersion, which is replaced directly and converted to carbon dioxide to dissipate in the air. Thus, ligand replaces the carbonate and coordinates on the surface of the zirconia nanoparticles to disperse the zirconia nanoparticles in different solvents. Also, the zirconia nanoparticles with the carbonate coordinated thereon can be stored in solid form, and the content of the zirconia in the solid form is higher than the content of the zirconia in the sol form, e.g., zirconia dispersed in the hydrosol or the toluene-sol. The solid form will decrease the costs for transportation and storage significantly. More importantly, the zirconia nanoparticles of the present disclosure have excellent dispersibility, and the particle sizes of the zirconia nanoparticles are between 1 nm and 10 nm. Because the surface of the zirconia nanoparticles is protected by the carbonate, the irreversible aggregation will not occur. Therefore, the zirconia nanoparticles provided by the present disclosure increase the specific surface area and reduce the sintering temperature when preparing precision ceramic appliances.

It will be apparent to those skilled in the art that various modifications and variations can be made to the structure of the invention without departing from the scope or spirit of the invention. In view of the foregoing, it is intended that the invention cover modifications and variations of this invention provided they fall within the scope of the following claims.

What is claimed is:

1. A method of preparing a zirconia nanoparticle material, comprising:
   providing an organic-free solvent;
   dispersing a precursor in the organic-free solvent to obtain an aqueous mixture, the precursor comprising zirconium hydroxide and sodium carbonate;
   heating the aqueous mixture at about 90° C. to 120° C. for about 4 hours to 12 hours; and
   recovering solids in the aqueous mixture to obtain zirconia nanoparticles having carbonate coordinated thereon.

2. The method of claim 1, wherein the precursor further comprises at least one of sodium hydroxide and sodium chloride.

3. The method of claim 1, wherein a molar ratio of the sodium to the carbonate is no less than 2.6.

4. The method of claim 1, wherein recovering the solids in the aqueous mixture comprises:
   separating the solids from the aqueous mixture;
   washing the solids with water, acetone, carbonic acid, ammonium bicarbonate, or a combination thereof; and
   drying the solids.

5. The method of claim 1, further comprising replacing the carbonate with an organic ligand or an inorganic ligand, wherein the organic ligand or the inorganic ligand is coordinated on the surface of the zirconia nanoparticles.

* * * * *